US009115188B2

(12) United States Patent
Qian et al.

(10) Patent No.: US 9,115,188 B2
(45) Date of Patent: Aug. 25, 2015

(54) MONOCLONAL ANTIBODIES SPECIFIC TO HEMAGGLUTININ FROM INFLUENZA VIRUS H5-SUBTYPE AND USES THEREOF

(71) Applicants: TEMASEK LIFE SCIENCES LABORATORY LIMITED, Singapore (SG); NATIONAL INSTITUTE OF HEALTH RESEARCH AND DEVELOPMENT (NIHRD)-MINISTRY OF Health of the Republic of Indonesia, Jakarta Pusat (ID)

(72) Inventors: Hong Liang Qian, Singapore (SG); Fang He, Singapore (SG); Siti Fadilah Supari, Jakarta Pusat (ID); Hwei-Sing Kwang, Singapore (SG)

(73) Assignees: Temasek Life Sciences Laboratory Limited, Singapore (SG); National Institute of Health Research and Development (NIHRD)-Ministry of Health of the Republic of Indonesia, Jakarta Pusat (ID)

( * ) Notice: Subject to any disclaimer, the term of this patent is extended or adjusted under 35 U.S.C. 154(b) by 108 days.

(21) Appl. No.: 13/897,725

(22) Filed: May 20, 2013

(65) Prior Publication Data

US 2013/0251715 A1 Sep. 26, 2013

Related U.S. Application Data

(62) Division of application No. 12/677,609, filed as application No. PCT/SG2008/000313 on Aug. 26, 2008, now Pat. No. 8,444,986.

(60) Provisional application No. 60/972,087, filed on Sep. 13, 2007.

(51) Int. Cl.
*A61K 39/42* (2006.01)
*C12Q 1/70* (2006.01)
*C07K 16/10* (2006.01)
*G01N 33/53* (2006.01)
*G01N 33/569* (2006.01)

(52) U.S. Cl.
CPC ...... *C07K 16/1018* (2013.01); *G01N 33/56983* (2013.01); *A61K 39/42* (2013.01); *C07K 2316/96* (2013.01); *C07K 2317/24* (2013.01); *C12N 2760/16111* (2013.01); *G01N 2333/11* (2013.01)

(58) Field of Classification Search
None
See application file for complete search history.

(56) References Cited

FOREIGN PATENT DOCUMENTS

| WO | 2007/089753 A2 | 8/2007 |
| WO | 2008/028946 A2 | 3/2008 |
| WO | 2008/140415 A1 | 11/2008 |
| WO | 2008/156763 A2 | 12/2008 |

OTHER PUBLICATIONS

Chen et al., 2007 J Vet Diagn Invest vol. 19, pp. 155-160.*
Smirnov et al. Acta Virologica 1999 vol. 43, pp. 237-244.*
Fang, Z. et al., "Preparation and Identification of a Single-Chain Antibody Fragment Against High Pathogenic H5N1 Avian Influenza Virus," Mar. 2007, Abstract only, XP002593444, Database accession No. NLM17460904, 1 page.
Sheng, W., Chinese Journal of Biotechnology, Mar. 2007, LNKD-PubMed:17460904, vol. 23, No. 2, Mar. 2007, pp. 292-296.
Luo, Hai-Feng et al., "characterization of a Broad-Spectrum Neutralization Monoclonal Antibody Against Haemagglutinin of H5 Subtype Avian influenza Virus," Bingdu Xuebao,—Chinese Journal of Virology, Zhongguo Weishgwu Xuchui, Beijing, CN, vol. 23, No. 2, Mar. 1, 2007, pp. 85-90, XP001525197, Abstract only, 1 page.
Simmons, C.P. et al., "Prophylactic and Therapeutic Efficacy of Human Monoclonal Antibodies Against H5N1 Influenza," PLOS Medicine, May 2007, LNKD-PubMed:17535101, vol. 4, No. 5, May 2007, p. E178, XP002593445, 9 pages.
Smirnov, Y.A. et al., "InfluenZa H5 Virus 21, 22 Escape Mutants: Immune Protection and Antibody Production in Mice," Virus Research Feb. 2004 LNKD-PubMed: 14749187, vol. 99, No. 2, Feb. 2004, pp. 205-208, XP00259346.
Communication, European Extended Search Report dated Mar. 19, 2012, Reference: HB/P42056EP, Application No./ Patent No. 08830488.6-1222 / 2207804 PCT/SG2008000313, 15 pages.
Hanson, Brendon J. et al., "Passice immunoprophylaxis and therapy with humanized monoclonal antibody specific for influenza A H5 hemagglutinin in mice," Respiratory Research, Oct. 2006, vol. 7, No. 126, 10 pages.
He, Qigai et al., "Detection of H5 Avian Influenca Viruses by Antigen-Capture Enzyme-Linked Immunosorbent Assay Using Monoclonal Antibody," Clinical and Vaccine Immunology, May 2007, vol. 14, No. 5, pp. 617-623.
Kaverin, Nikolai V. et al., "Epitope Mapping of Hemagglutinin Molecule of a High Pathogenic H5N1 Influenza Virus by Using Monoclonal Antibodies," Journal of Virology, Dec. 2007, vol. 81, No. 23, pp. 12911-12917.
Intellectual Property Office of Singapore (IPOS), Written Opinion and Search Report dated Sep. 16, 2011, Singapore Patent Application No. 201001723-4, "Monoclonal Antibodies Specific to Hemagglutinin From Influenza Virus H5-Subtype and Uses Thereof," 12 pages.
Smirov, Y.A., et al., "Prevention and treatment of bronchopneumonia in mice caused by mouse-adapted variant of avian H5N2 influenza A virus using monoclonal antibody against conserved epitope in the HA stem region, " Archives of Virology, 145: 1733-1741 (2000).
Smirnov, Y.A., et al., "An epitope shared by the hemagglutinins of H1, H2, H5 and H6 subtypes of influenza A virus," Acta virologica 43: 237-244 (1999).
Nettles, Victor F., et al., Wildlife Surveillance Associated with an Outbreak of Lethal H5N2 Avian Influenza in Domestic Poultry, Avian Diseases, 29(3): 733-741 (1985).

(Continued)

*Primary Examiner* — Mary E Mosher
*Assistant Examiner* — Myron Hill
(74) *Attorney, Agent, or Firm* — Rothwell, Figg, Ernst & Manbeck P.C.

(57) ABSTRACT

Monoclonal antibodies and related binding proteins that are specific for conformational epitopes of avian influenza virus H5 subtype hemagglutinin glycoprotein are provided. The antibodies can be used for the detection and treatment of H5 subtype AIV in specimens.

23 Claims, 2 Drawing Sheets

(56) References Cited

OTHER PUBLICATIONS

Veits, Jutta et al., "Newcastle disease virus expressing H5 hemagglutinin gene protects chickens against Newcastle disease and avian influenza," Proceedings of the National Academy of Sciences (USA), 103(21): 8197-8202 (May 23, 2006).

Suarez, D.L., et al., "Immunology of avian influenza virus: a review," Developmental and Comparative Immunology, 24: 269-283 (2000).

Kirkca, L.J., "Principles of Immunochemical Techniques," in Burtis, C.A., et al., Tietz Textbook of Clinical Chemistry and Molecular Diagnostics 4th Edition, St. Louis, MIssouri: Elsevier Saunders, 2006. Chapter 9, pp. 219-243.

Harlow, E. and Lane, D., Antibodies: A Laboratory Manual. USA: Cold Springs Harbor Laboratory, 1988, chapters 5-9.

Horthongkham, Navin, et al., "Specific antibody response of mice after immunization with COS-7 cell derived avian influenza virus (H5N1) recombinant proteins," Journal of Immune Based Therapies and Vaccines, 5, Article 10, (Oct. 3, 2007), 5 pages.

Laddy, Dominick J., et al., "Heterosubtypic Protection against Pathogenic Human and Avian Influenza Viruses via In Vivo Electroporation of Synthetic Consensus DNA Antigens," Plus ONE, 3(6):e2517 (2008) 8 pages.

Chen, Jianfeng, et al., "A latex agglutination test for the rapid detection of avian influenza virus subtype H5N1 and its clinical application," J. Vet Diagn. Invest, 19:155-160 (2007).

\* cited by examiner

MONOCLONAL ANTIBODIES SPECIFIC TO HEMAGGLUTININ FROM INFLUENZA VIRUS H5-SUBTYPE AND USES THEREOF

CROSS-REFERENCE TO RELATED APPLICATIONS

The present application is a division of U.S. patent application Ser. No. 12/677,609 filed 21 Jul. 2010 which in turn is a filing under 35 USC 371 of PCT/SG2008/000313 filed 26 Aug. 2008, which in turn claims priority to U.S. Provisional Application Ser. No. 60/972,087 filed 13 Sep. 2007. Each application is incorporated herein in its entirety.

FIELD OF THE INVENTION

This invention relates to antibodies and related binding proteins for the detection and treatment of avian influenza virus ("AIV"). More particularly, this invention relates to monoclonal antibodies and related binding proteins useful for the detection and treatment of the highly pathogenic H5 subtypes of AIV and to methods and products for the diagnosis, surveillance and treatment of AIV infections in animals and humans.

BACKGROUND OF THE INVENTION

H5N1 avian influenza virus may become the cause of the next flu pandemic. Annual outbreaks of influenza A infection are an ongoing public health threat and novel influenza strains can emerge periodically to which humans have little immunity, resulting in devastating pandemics. The "Spanish flu" pandemic of 1918, caused by the H1N1 influenza virus, killed more than 40 million people world-wide. The origin of H1N1 may have gone directly from birds to humans, or it may have involved incubation in an intermediate host, such as the pig or another, as yet unidentified, animal host (1). (A bibliography is provided at the end of the disclosure.) Both the 1957 pandemic and the 1968 pandemic, caused by the H2N2 and H3N2 influenza viruses, respectively, likely originated as reassortments in which one or both human-adapted viral surface proteins were replaced by proteins from avian influenza strains (2).

The H5N1 virus has the ability to infect an unprecedented range of hosts, including carnivores. The first confirmed instances of AIV H5N1 infecting humans took place in 1997. Highly pathogenic H5N1 infections occurred in both poultry and humans. This was the first time an avian influenza virus transmission directly from birds to humans had been found. Thereafter, according to the World Health Organization (WHO), the total number of human H5N1 cases, since the initial outbreaks in south-east Asia which occurred in 2003, has reached 281, with 169 deaths. Indonesia reported its first human case of avian flu caused by the H5N1 virus in June of 2005. To date, it is the only country to report cases in 2007, with 81 confirmed human cases, 63 of which were fatal, as of March, 2007.

Influenza viruses are classified according to their nucleoprotein and matrix protein antigenic specificity. These viruses are categorized mainly into A, B and C serotypes, with type A having eight RNA segments that encode ten viral proteins. All known type A influenza viruses originated in birds. This category of virus can infect other species, such as horses, pigs, owls and seals, and poses a threat to humans as well (23). Influenza A virus is further divided into subtypes according to the antigenic nature of the envelope glycoproteins, hemagglutinins ("HAs"), H1 through H16, and neuraminidases ("NAs"), N1 through N9 (24, 25, 26). It is believed that proteolytic cleavage of HA protein at the HA1-HA2 junction is related to the pathogenicity in avian strain and that the presence of hydrophobic amino acids around this cleavage site are characteristic of the H5 subtype. In addition, the HA protein is believed to mediate attachments to host cell sialoside receptors and subsequent entry by membrane fusion (27), and HA protein is thought to serve as a primary target for neutralizing antibodies (26).

Testing during an outbreak of an acute respiratory disease can determine if influenza is the cause. During influenza season, testing of selected patients presenting with respiratory illnesses compatible with influenza can help establish whether influenza is present in a specific patient population and help health-care providers determine how to use their clinical judgment for diagnosing and treating respiratory illness. A rapid influenza test helps in the determination of whether to use an antiviral medication. Some tests, such as a viral culture, reverse-transcriptase polymerase chain reaction (RT-PCR) and serological testing are the routine methods, but results may not be available in a timely manner to assist clinicians (3). At present, most of the rapid diagnostic tests currently in use are monoclonal antibody-based immunoassays (3, 4, 5). Immunofluorescence (fluorescent antibody staining) is the alternative to rapid influenza diagnostic tests which can be used in many hospital laboratories and generally can yield test results in 2-4 hours. Above all, specific monoclonal antibody generation is fundamental to most currently used rapid, sensitive and cost-effective diagnostic methods.

The identification of regionally distinct sublineages has indicated that the H5N1 virus is geographically broad with great genetic and antigenic diversity. Phylogenetic analysis showing that all viruses from Indonesia form a distinct sublineage of H5N1 genotype Z viruses suggests that this outbreak likely originated from a single introduction that spread throughout the country (14, 15). It would be very useful to have available monoclonal antibodies which specifically recognize Indonesia influenza isolates. It further would be useful to have available such mAbs which also cover Vietnam and Singapore influenza isolates.

OBJECTS OF THE INVENTION

An object of this invention is to provide monoclonal antibodies ("mAbs") and related binding proteins that bind specifically to H5 subtypes of AIV, particularly to H5 Indonesia AIV isolates. The specificity of monoclonal antibody responses provides a basis for an effective diagnostic reagent. MAbs and binding proteins derived therefrom also can be useful as therapeutic agents.

SUMMARY OF THE INVENTION

In accordance with the present invention, monoclonal antibodies and related binding proteins that are specific for conformational epitopes of the H5 subtype hemagglutinin glycoprotein are provided. MAbs that target conformational epitopes are useful for detecting the virus in tissues which have not been pre-treated, such as frozen tissue specimens and other biological tissues and fluids. In particular, a mAb designated 3B1 targets H5N1 hemagglutinin from all 25 known H5 AIV isolates from Indonesia. A second mAb, designated 3E8, targets H5N1 hemagglutinin from all but one of these AIV isolates. MAb 3B1 also binds to H5N2 and H5N1/PR8.

Accordingly, this invention comprises a binding protein having substantially the immunological binding characteristics for a conformational H5-subtype hemagglutinin epitope as those of mAb 3B1 or 3E8.

In a further aspect, the invention comprises a method for detecting H5 subtype AIV in a specimen which comprises detecting the binding of AIV with a mAb or binding protein having substantially the immunological binding characteristics of mAb 3B1 or 3E8. In particular, the invention relates to immunofluorescence assays, immunohistochemical assays and ELISA methods that utilize such binding proteins. The invention further comprises a method for verifying that the H5 subtype AIV in the specimen is H5N1 by additionally detecting the binding of the virus sample with a binding protein having substantially the immunological binding characteristics of a mAb which binds to neuraminidssase glycoprotein of n1-subtype AIV.

In another aspect, the invention relates to kits for the detection of AIV which comprise binding proteins having substantially the immunological binding characteristics of mAb 3B1 or 3E8. The kits can further comprise a binding protein having substantially the immunological binding characteristics of a mAb which binds to neuraminidase glycoprotein of N1-subtype AIV.

The invention further relates to methods of treating subjects infected with an H5 AIV strain, such as an H5N1 AIV strain, which comprise administering to such subjects effective amounts of one or more recombinant monoclonal antibodies or binding proteins or fragments thereof having substantially the immunological binding characteristics of mAb 3B1 or 3E8. Such recombinant antibodies or antibody fragments desirably comprise the variable region but not the constant region of mAbs 3B1 or 3E8.

BRIEF DESCRIPTION OF THE DRAWINGS

FIG. 1A is an image in which H5N1 is detected in MDCK cells. In FIG. 1B, the merge of ultraviolet light and normal light indicated the individual cells infected by virus compared to uninfected cells. There was no fluorescence signal on MDCK cells without virus infection as shown in FIG. 1C. FIG. 1D shows the merge of ultraviolet light and normal light on the same cells as in FIG. 1C.

In FIG. 2A, MDCK cells were stained with FITC fluorescence after monoclonal antibodies neutralized H5N1 virus infection. In FIG. 2B, MDCK cells were stained with FITC fluorescence without monoclonal antibody neutralization of H5N1 virus infection.

DETAILED DESCRIPTION OF THE INVENTION

Figure 1:
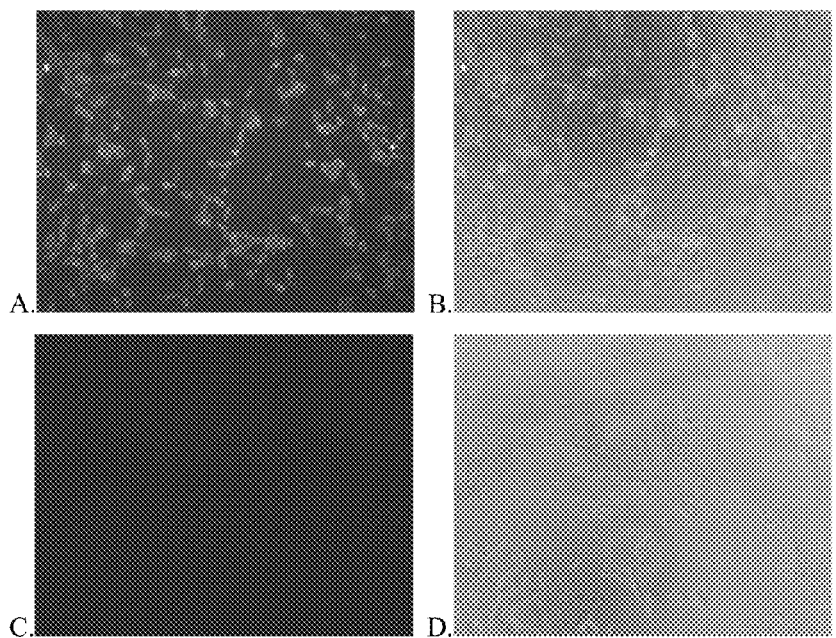
FIGS. 1A-1D are representative IFA images comparing MDCK cells infected with AIV H5N1 against MDCK cells without virus infection.

The present invention is directed to mAbs and related antigen-binding proteins that bind specifically to the hemagglutinin envelope glycoprotein of H5 subtype of AIV. In particular, the mAb or related antigen binding protein possesses the immunological binding characteristics of mAb 3B 1, as produced by hybridoma 3B 1, deposited with the American Type Culture Collection (ATCC) on Mar. 20, 2007, and assigned Accession Number PTA-8247, or mAb 3E8, as produced by hybridoma 3E8, deposited with the ATCC on Jul. 10, 2007, and assigned Accession Number PTA-8527. The invention further embodies these hybridomas and provides a continuous source of the mAbs and binding proteins of the invention.

The invention further relates to methods for the detection and diagnosis of H5 subtype AIV infection and assay kits that comprise the mAbs or binding proteins of the invention. In a preferred embodiment, the invention further relates to methods of verifying that the H5 subtype AIV infection is H5N1 subtype AIV infection and assay kits for making such determination. Such diagnostic methods can comprise the use of mAb or related antigen binding protein having the immunological binding characteristics of mAb 3B1 or 3E8 in combination with a mAb or related antigen binding protein which recognizes neuraminidase glycoprotein of N1 subtype AIV. One mAb which binds to a conformational epitope of neuraminidase from all or essentially all H5N1 isolates from Indonesia is mAb 6C6, deposited with the ATCC on Jul. 10, 2007, and assigned Accession Number PTA-8526. Kits can comprise a mAb or binding protein of the invention which binds to H5 subtype hemagglutinin glycoprotein and a mAb or binding protein which binds to N1 subtype neuraminidase glycoprotein.

The invention further relates to methods of treating a subject infected with an H5 AIV strain through the administration of effective amounts of an antibody fragment or recombinant antibody comprising the variable region of one or more antibodies or related binding proteins of the invention. In particular, in this embodiment the subject is infected with an Indonesian isolate of H5N1 subtype of AIV. The antibodies of this invention also can be administered to subjects on the advent of a possible influenza pandemic as a precautionary measure. In this instance, effective amounts of antibodies to be administered are about half of the amounts used to treat H5 AIV infections.

Various terms are used herein, which have the following meanings:

The term "immunological binding characteristics" of a mAb or related binding protein, in all of its grammatical forms, refers to the specificity, affinity and cross-reactivity of the mAb or binding protein for its antigen.

The term "conformational epitope" refers to a mAb or related binding protein binding site that exists in the H5-subtype hemagglutinin glycoprotein in its native three-dimensional form.

The term "binding protein" refers to a protein, including those described below, that includes the antigen binding site of a mAb of the present invention or a mAb having the immunological binding characteristics of a mAb of the present invention.

The present invention advantageously provides methods for preparing monoclonal antibodies having the binding characteristics of mAb 3B1 by immunizing an animal with an Indonesian isolate of AIV subtype H5N1 or preparing monoclonal antibodies having the binding characteristics of mAb 3E8 by immunizing an animal with an Indonesian isolate of AIV subtype H5N1. Any such antigen can be used as an immunogen to generate antibodies with the desired immunological binding characteristics. Such antibodies include, but are not limited to, monoclonal antibodies, chimeric antibodies, single chain antibodies, Fab fragments and proteins comprising the antigen binding sequence of mAb 3B1 or 3E8.

The mAbs of the present invention can be produced by any technique that provides for the production of antibody molecules by continuous cell lines in culture. Such methods include, but are not limited to, the hybridoma technique originally developed in 1975 by Kohler and Milstein (*Nature* 256:495-497), as well as the trioma technique, the human B-cell hybridoma technique (Kozbor et al., 1983, *Immunology Today* 4:72) and the EBV-hybridoma technique to produce human monoclonal antibodies (Cole et al., in *Mono-* clonal Antibodies and Cancer Therapy Alan R. Liss, Inc., pp 77-96 (1985)). Human antibodies can be used and can be obtained by using human hybridomas (Cote et al., 1983, *Proc. Nat'l. Acad. Sci. U.S.A.*, 80:2026-2030) or by transforming human B cells with EBV virus in vitro (Cole et al., 1985, in *Monoclonal Antibodies and Cancer Therapy*, Alan R. Liss, pp. 77-96). Moreover, techniques developed for the production of "chimeric antibodies" or "humanized antibodies" (Morrison et al., 1984, *J. Bacteriol.* 159-870; Neuberger et al., 1984, *Nature* 312:604-608; Takeda et al., 1985, *Nature* 314: 452-454) by introducing sequences from a murine antibody molecule of the present invention, e.g., mAb 3B1 or 3E8, together with genes from a human antibody molecule of appropriate biological activity can be used. Chimeric antibodies are those that contain a human Fc portion and a murine (or other non-human) Fv portion. Humanized antibodies are those in which the murine (or other non-human) complementarity determining regions (CDR) are incorporated into a human antibody. Both chimeric and humanized antibodies are monoclonal. Such human or humanized chimeric antibodies are preferred for use in in vivo diagnosis or therapy of human diseases or disorders.

According to the invention, techniques described for the production of single chain antibodies (U.S. Pat. No. 4,946, 778) can be adapted to provide single chain antibodies of the present invention. An additional embodiment of the invention utilizes the techniques described for the construction of Fab expression libraries (Huse et al., 1989, *Science* 246: 1275-1281) to allow rapid and easy identification of monoclonal Fab fragments with the desired specificity for an antibody of the present invention, or its derivatives, or analogs.

Antibody fragments that contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent. Such antibody fragments can be generated from any of the polyclonal or monoclonal antibodies of the invention.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), immunofluorescence assays and immunoelectrophoresis assays, etc. In one embodiment, antibody binding is detected by detecting a label on the primary antibody. In another embodiment, the primary antibody is detected by detecting binding of a secondary antibody or other reagent to the primary antibody. In a further embodiment, the secondary antibody is labeled. Means are known in the art for detecting binding in an immunoassay and are within the scope of the present invention.

The foregoing antibodies can be used in methods known in the art relating to the detection or localization of the H5 subtype of AIV, e.g., Western blotting, ELISA, radioimmunoassay, immunofluorescence assay, immunohistochemical assay, and the like. The techniques disclosed herein may be applied to the qualitative and quantitative determination of the H5 subtype of AIV and to the diagnosis and surveillance of animals or humans infected with the virus.

The present invention also includes assay and test kits for the qualitative and/or quantitative determination of the H5 subtype of AIV. Such assay systems and test kits may comprise a labeled component prepared, e.g., by labeling with a radioactive atom, a fluorescent group or an enzyme, coupling a label to the mAb or related binding protein of the present invention, or to a binding partner thereof. Such assay or test kits further may comprise reagents, diluents and instructions for use, as is well known to those skilled in immunoassay techniques.

In certain embodiments of the invention, such kits will contain at least the mAb or related binding protein of the invention, means for detecting immunospecific binding of said mAb or related binding protein to AIV in a biological sample, and instructions for use, depending upon the method selected, e.g., "competitive," "sandwich," "DASP" and the like. The kits may also contain positive and negative controls. They may be configured to be used with automated analyzers or automated immunohistochemical slide staining instruments.

An assay kit of the invention may further comprise a second antibody or binding protein that may be labeled or may be provided for attachment to a solid support (or attached to a solid support). Such an antibody or binding protein may be, for example, one that binds to AIV. Such second antibodies or binding proteins may be polyclonal or monoclonal antibodies.

Monoclonal antibodies to H5-subtype hemagglutinin protein may be prepared by immunizing animals with AIV or H5 protein or fragments thereof. A preferred method involves amplification of the H5-subtype HA1 gene followed by expression of the gene, recovery and purification of H5 subtype recombinant proteins and use of the purified proteins as immunogens. For example, H5N1 AIV is propagated by inoculation of chicken embryos with available strains of the virus, followed by isolation of the viral RNA. The HA1 gene is amplified by reverse transcriptase polymerase chain reaction (RT-PCR) and then may be cloned into a baculovirus vector that is used to express H5 proteins in insect cells. The proteins so produced then can be used to immunize mice or other suitable species for production of hybridomas.

Hybridomas are screened for their ability to produce high affinity mAbs that are capable of specifically binding to H5 proteins and distinguish them from other AIV subtypes. In accordance with the invention, it has been found that antibodies with virus neutralization ability are able to recognize conformational epitopes in the H5-subtype hemagglutinin protein. This finding resulted from the generation of virus escape mutants in the presence of each neutralizing mAb after 1-2 rounds of selection in Madin-Darby canine kidney (MDCK) cells. The HA1 gene was cloned from these neutralization escape mutants by RT-PCR and sequenced to identify point mutations. In this panel of antibodies, 2 neutralization epitopes were found in mAbs 3B1 and 3E8. Neutralization-escape ability was confirmed using hemagglutination inhibition assays.

HA1 contains 338 amino acids. To study the distribution of linear epitopes on the protein, truncated and mutated fragments are advantageously tested for binding with mAbs, e.g., by Western blot or a similar technique. Linear epitopes may be identified that are binding targets for mAbs that give a good performance in detecting denatured H5 subtype protein, such as that occurring in formalin-fixed tissue, using immunohistochemical staining methods. Mapping of the H5 subtype mAbs in this manner provides a platform for further study and a more effective clinical diagnosis of the infectious H5N1 AIV.

The present invention also has provided a better understanding of the antigenic structure of the hemagglutinin molecule of H5-subtypes of AIV. The mAbs and related binding proteins of the invention provide a means for detecting this highly pathogenic virus in frozen sections and biological specimens.

MAbs 3B1 and 3E8 are highly efficacious on frozen tissue sections but do not detect antigen in formalin-fixed tissues. Monoclonal antibodies 3B 1 and 3E8 were determined by epitope mapping to target conformational epitopes of the H5N1 virus. These antibodies were able to bind and to recognize these viral antigens without prior treatments to the tissue sections.

This invention provides convenient, highly specific and sensitive means for detecting H5 subtype AIV. One such means is the ELISA format. Each of MAb 3B1 and 3E8 can be used as a capture antibody, either alone or in combination. If used alone, the selected antibody can be used as the capture antibody and that same antibody conjugated with horseradish peroxidase (HRP) can be used as detecting antibody.

Other immunological methods to detect H5 viruses include, for example, dot-blot and in situ hybridization formats.

The preferred ELISA test of this invention is able to detect HA antigen from H5N1 avian influenza virus infecting poultry and humans in Indonesia, indicating the utility of the invention for detecting both avian and human H5 infections.

The H5-subtype mAbs of this invention have advantages over other current methodologies as diagnostic tools. First, the mAbs are highly specific for the highly infectious H5-subtype AIV. Such highly specific monoclonal antibodies represent a breakthrough in the field of avian influenza diagnosis. Prior to the present invention, no monoclonal antibody has been reported that could detect all, or nearly all, Indonesian H5N1 viruses. The monoclonal antibodies of the present invention can recognize all, or essentially all, of the H5N1 viruses collected in Indonesia within the last two years. Additionally, these mAbs provide a safe and convenient diagnostic approach for the detection of H5 AIV. Frozen section slides can be cryogenically stored for long periods of time and facilitate further diagnosis and surveillance of infections. The antibodies are useful for diagnosis and for the preparation of recombinant antibodies for treatment, and as such will be very useful tools in restraining a potential flu pandemic.

Another embodiment of the invention relates to neutralization escape mutants of H5 avian influenza. The term "neutralization escape mutant" refers to a mutant virus raised by point mutations in the genes encoding hemagglutinin which caused antigenic drift in the H5 virus and affect neutralization epitopes. A neutralization escape mutant can evade neutralization by certain monoclonal antibodies that are effective in neutralizing its parent virus. In manual screening for escape mutants, a parental virus is incubated with a certain neutralization antibody and inoculated into a host, such as MDCK cells or chicken embryos. After 2-3 rounds of screening, the escape mutant for the neutralization mAb is cloned and subjected to HA1 gene sequencing. The mutated amino acid is determined by alignment with the parental virus sequence, and the mutated site indicates one of the amino acids comprising the neutralization epitope recognized by the neutralization mAb.

In the present invention, 3B1 escape mutants arise from H5N1 AIV (A/Indonesia/CDC669/2006 (H5N1)) (GenBank Accession #CY014481; GenBank GI #113497155) by the 3B1 neutralization monoclonal antibody. 3E8 escape mutants arise from the same strain of H5N1 AIV by the 3E8 neutralization antibody. Mutation sites are listed in Example 3, Table 4, below.

Neutralization escape mutants are different from their parental virus in that they no longer can be recognized by certain neutralization antibodies which specifically bind to the parent virus. In view of this, these mutants can be used to immunize mice for new monoclonal antibody production in accordance with the teachings above. Among the new mAbs, a monoclonal antibody which exactly recognizes the mutated epitope can be screened out and then can be used to provide complementary surveillance to avian influenza viruses other than the parental virus. By repeating this process through several generations, further escape mutants can be found and further neutralizing antibodies obtained. These antibodies can be used in the methods of the present invention.

In a further embodiment of the invention, the antibodies and related binding proteins of the invention can be administered to treat subjects suffering from an H5 AIV infection, particularly an infection from an H5N1 subtype of AIV. The antibodies and related binding proteins of the invention also can be administered to subjects as a preventive measure in the event of an influenza pandemic or threatened pandemic. The antibodies and related binding proteins can be administered in a single dose or in repeated administrations, optionally in a slow release form. Administration can be made by any means that enables the antibody to reach its site of action in the body of the subject being treated, e.g., intravenously, intramuscularly, intradermally, orally or nasally. Typically, the antibody is administered in a pharmaceutically acceptable diluent or carrier, such as a sterile aqueous solution, and the composition can further comprise one or more stabilizers, adjuvants, solubilizers, buffers, etc. The exact method of administration, composition and particular dosage will be determined and adjusted at the time of therapy, depending upon the individual needs of the subject, taking into account such factors as the subject's age, weight, general health, and the nature and extent of his or her symptoms, as well as the frequency of treatment to be given. Generally, the dosage of antibody administered is within the range of about 0.1 mg/kg to about 1 mg/kg body weight when the antibody is administered to treat patients suffering from an H5 AIV infection. Typically, the dosage is reduced by about half, i.e. to within the range of about 0.05 mg/kg to about 0.5 mg/kg body weight, when administered as a preventive measure.

A single recombinant antibody or binding protein of the invention can be administered for therapeutic purposes or a combination of two or more can be administered. If antibodies to one or more generations of neutralization escape mutants have been produced, such antibodies and the 3B1 and/or 3E8 antibodies described above can be administered as therapeutic antibody "cocktails."

The following examples are provided to illustrate a preferred mode of practicing the invention. The invention is not limited to the details of the examples, but is commensurate with the full scope of the appended claims.

EXAMPLE 1

Production of Hybridomas

All live H5N1 influenza viruses, except H5N1/PR8, were obtained from Indonesia. H5N1/PR8 was obtained from the Center for Disease Control (USA). It is a non-pathogenic recombinant virus that contains the HA and NA genes of an AIV H5N1 virus that infected a human in Vietnam (A/Vietnam/1203/2004). H5N2 (A/chicken/Singapore/98) and H7N1 (A/chicken/Singapore/94) were obtained from Agri-Food & Veterinary Authority (AVA) of Singapore. These virus stocks were used to infect 9 and 11 day old embryonated chicken eggs (Chew's Poultry Farm, Singapore) and allowed to replicate for two generations. Then, allantoic fluid was drawn and viral titer was determined using hemagglutinin assay (HA). Inactivated H5N1 (A/goose/guangdong/97) was used for RNA extraction to amplify HA1 gene by RT-PCR. Madin Darby kidney cells (MDCK, ATCC CCL34) cells were grown in DMEM media with 10% FBS at 37° C. with 5% $CO_2$.

Purification of the viruses was performed by centrifugation of virus-containing allantoic fluids at 10,000 rpm for 30 minutes to remove debris, followed by ultracentrifugation of the supernatant at 40,000 rpm for 3 hours. The virus pellet was suspended in PBS.

Monoclonal antibodies were purified from clarified fluids using protein A affinity column (Sigma Aldrich; St. Louis, Mo., USA) and Immunopure® IgM purification kit (Pierce Biotechnology; Rockford, Ill., USA) in accordance with manufacturer's instructions. The antibody concentrations were measured by using an ND-1000 spectrophotometer (NanoDrop Technologies; Wilmington, Del., USA).

BALB/c mice were immunized with inactivated avian influenza virus of A/Indonesia/chicken/H5N1 with the oil adjuvant Montanide ISA563 (Seppic, France) in a volume of 0.2 ml. Intraperitoneal injections were delivered on days 0, 14, 28 and 42. Splenocytes from immunized mice and myeloma cells (SP2/0) were collected and fused as described by De St. Groth and Scheidigger to produce hybridomas (16). After selection with hypoxanthine-aminopterin-thymidine (HAT) medium, culture media from the hybridomas showing significant growth after 14 days were tested for the presence of specific antibodies against A/Indonesia/chicken/H5N1 infected MDCK cells by immunofluorescence assay (IFA). Selected hybridomas were cloned by limiting dilution, re-identified, cloned a second time, and retested by IFA. Once established, the hybridoma line was propagated in tissue culture and frozen in liquid $N_2$ for future use.

EXAMPLE 2

Screening of mAbs by IFA

Immuno-fluorescence assay was used to verify the interaction between an antibody and the antigen target. MDCK cells which had been infected with influenza virus isolate A/Indonesia/chicken/H5N1 overnight were rinsed with PBS-T (0.05% Tween-20 in PBS, pH 7.4) in 96 well plates. The cells were fixed by incubating them in pre-cooled 100% ethanol for 10 minutes. The cells were washed in PBS-T 3 times, then incubated in 1% BSA, PBS-T for 30 minutes to block unspecific binding of the antibodies. They then were incubated with 100 µL of hybridoma culture fluid in wells of 96-well plates for 2 hours at room temperature or overnight at 4° C. The cells were washed with PBS-T and incubated with secondary antibodies, fluorescently labeled goat/rabbit anti-mouse antibodies (DakoCytomation, Carpenteria, Calif.), at a dilution of 1:100 in 1% BSA, PBS-T, for 60 minutes at room temperature. The wells were washed with PBS-T. The PBS-T was discarded and 50% glycerol in PBS was added. Fluorescence signals were checked under a microscope with ultraviolet light.

Uninfected MDCK cells were used as negative controls. Serum from a mouse immunized with inactivated H5N1 virus was used as a positive antibody control. By comparing MDCK cells incubated with the respective hybridoma supernatants with the controls, the hybridoma supernatants which gave positive staining were selected for cloning by limiting dilution. Stable mAb-producing hybridomas were obtained by this procedure.

An antibody designated mAb3B 1 was found to bind to H5N1 hemagglutinin from all 25 isolates from Indonesia. MAb 3E8 was found to bind to all but one of those isolates, A/Indonesia/CDC594/2006 (H5N1). MAb 3B1 also was positive in the IFA with H5N1/PR8 and H5N2. The AIV strains reacted with these mAbs are listed in Table 6 at the end of the Examples section.

Representative IFA images are shown in FIG. 1.

EXAMPLE 3

Characterization of H5-Subtype mAbs

Isotyping of mAbs. Isotyping was performed using a mouse mAb isotyping kit (Amersham Bioscience, England) (data not shown). Both mAb 3B1 and 3E8 were determined as IgM.

Hemagglutination-Inhibition Test (HI). A constant amount of hemagglutinating (HA) antigen was added to each well in a microtiter plate (NUNC). The testing antibody then was placed in the first well and serially diluted. The plates were incubated for one hour and then chicken red blood cells (RBC) were added to each well. If antibody was present in the test serum the RBCs would not agglutinate with the HA antigen. HI negative wells would have a diffuse sheet of agglutinated RBCs covering the bottom of the well. HI positive wells would have a well-circumscribed button of unagglutinated RBCs.

MAb 3B1 in culture fluid had HI activity from 16 to 32 with diverse Indonesian H5N1 isolates and with H5N2 and only about 2 with H5N1/PR8. MAb 3E8 had no HI with Indonesian isolate CDC594, H5N2 or H5N1/PR8 but had HI in the range of 16 to 32 with all other Indonesian H5N1 isolates.

Virus micro-neutralization assay. MDCK cells were used for determination of 50% tissue culture infections dosage (TCID50). Antibodies with two-fold serial dilutions were added to 96-well cell culture plates. The diluted antibodies were mixed with an equal volume of diluent containing influenza virus at 100 $TCIS_{50}$/well. After a 2-hour incubation at 37° C. in a 5% $CO_2$ humidified atmosphere, 100 µl of MDCK cells at $1.5 \times 10^5$/ml were added to each well. The plates were incubated for 18 hours at 37° C. and 5% $CO_2$. The monolayers were washed with PBS and fixed in 100% ethanol for 10 minutes. The presence of viral protein was detected by ELISA with mouse sera against the influenza H5N1.

The ELISA was performed at room temperature. The fixed plates were washed 3 times with PBS-T (PBS containing 0.05% Tween 20). The mouse sera antibody diluted 1/500 in PBS-T containing 1% bovine serum albumin was added to each well and incubated at room temperature for 1 hour. The plates were washed four time in wash buffer and 100 µl of horseradish peroxidase-labeled goat anti-mouse immunoglobulin (DakoCytomation) diluted 1/2000 were added to each well. The plates were incubated for 1 hour at room temperature and then washed six times with wash buffer. One hundred microliters of freshly prepared substrate (10 mg of o-phenylenediamine dihydrochloride per 20 ml of 0.05M phosphate citrate buffer, pH 5.0, containing 0.03% sodium perborate) were added to each well and the plates were incubated at room temperature for approximately 5 minutes. The reaction was stopped with 50 µL of 2N sulfuric acid. The absorbance was measured at 490 nm ($A_{490}$) with an automated plate spectrophotometer (Mitenyi Biotec).

TABLE 1

| mAb 3B1 | mAb + Virus | | Virus | |
|---|---|---|---|---|
| | #1 | #2 | #3 | #4 |
| A/Indonesia/chicken/H5N1 | 0.569 | 0.632 | 1.187 | 1.213 |
| A/Indonesia/CDC7/H5N1 | 0.661 | 0.614 | 1.34 | 1.398 |
| A/Indonesia/CDC370/H5N1 | 0.791 | 0.825 | 1.669 | 1.712 |
| A/Indonesia/CDC594/H5N1 | 0.686 | 0.692 | 1.59 | 1.67 |
| A/Indonesia/CDC623/H5N1 | 0.267 | 0.281 | 1.178 | 1.041 |
| A/Indonesia/TLL008/H5N1 | 0.524 | 0.523 | 1.27 | 1.211 |
| A/Indonesia/TLL011/H5N1 | 0.279 | 0.288 | 0.634 | 0.73 |
| A/Indonesia/TLL012/H5N1 | 0.755 | 0.729 | 1.225 | 1.308 |
| H5N1/PR8 | 0.52 | 0.585 | 0.904 | 0.893 |
| DMEM Medium | 0.2 | 0.193 | 0.128 | 0.118 |

TABLE 2

| mAb 3E8 | MAb + Virus | | Virus | |
|---|---|---|---|---|
| | #1 | #2 | #3 | #4 |
| A/Indonesia/chicken/H5N1 | 0.625 | 0.679 | 1.387 | 1.26 |
| A/Indonesia/CDC7/H5N1 | 0.723 | 0.689 | 1.433 | 1.37 |
| A/Indonesia/CDC370/H5N1 | 0.9 | 0.919 | 1.519 | 1.509 |
| A/Indonesia/CDC594/H5N1 | 1.696 | 1.532 | 1.575 | 1.578 |
| A/Indonesia/CDC623/H5N1 | 0.978 | 0.936 | 1.629 | 1.583 |
| A/Indonesia/TLL008/H5N1 | 0.828 | 0.875 | 1.502 | 1.494 |
| A/Indonesia/TLL011/H5N1 | 0.42 | 0.384 | 0.72 | 0.702 |
| A/Indonesia/TLL012/H5N1 | 0.761 | 0.818 | 1.055 | 1.142 |
| H5N1/PR8 | 1.035 | 0.902 | 0.854 | 0.908 |
| DMEM Medium | 0.206 | 0.26 | 0.111 | 0.117 |

Tables 1 and 2 show that mAb3B1 and mAb 3E8 neutralized H5N1 isolates in infected MDCK cells. In the presence of monoclonal antibody, the ELISA reading results were reduced by approximately one half in comparison to those in the absence of antibody, suggesting that the virus particles had been neutralized on the infecting MDCK cells.

Because the ELISA reading had a high background while IFA is visible, the neutralization tests were done by the detect method of IFA on MDCK cells to confirm the neutralization ability of these monoclonal antibodies. MAb 3B1 could neutralize the infection of all H5N1 isolates, while mAb 3E8 could neutralize all isolates except for 594. These results were consistent with the IFA and HI test results.

Figure 2:
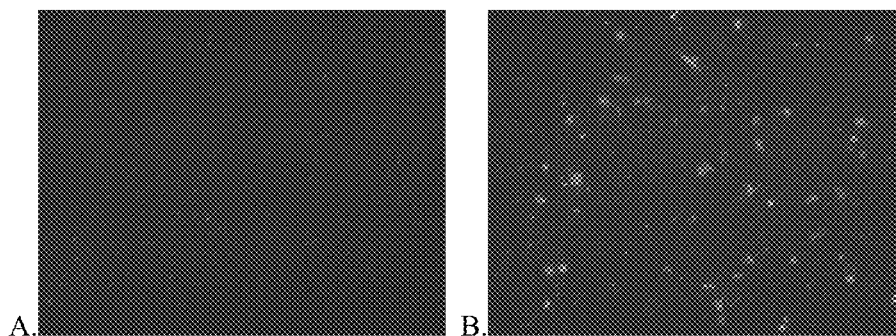
FIGS. 2A and 2B show monoclonal antibody neutralization activity of influenza virus on MDCK cells.

FIGS. 2A and 2B illustrate mAb neutralization activity on MDCK cells infected with AIV. FIGS. 2A and 2B show MDCK cells stained with FITC fluorescence subsequent to mAB neutralization of virus infection and absent mAb neutralization, respectively.

Titration of virus neutralization on MDCK cells and in chicken embryos. MDCK cells and 10-day old embryos were used for determination of 50% tissue culture infections dosage ($TCID_{50}$) and 50% embryo infectious dosage ($EID_{50}$), respectively. MDCK cells ($2 \times 10^4$/ml) were allowed to grow to 70%-90% confluence. Chicken embryos were infected with the respective viruses, using a series of dilution factors from $10^{-1}$ to $10^{-8}$, and the subsequent allantoic fluids were tested for $TCID_{50}$ and $EID_{50}$. The viruses then were used to infect both MDCK cells at their exponential phase (highest sensitivity to virus infection) and 10-day old chicken embryos. Uninfected MDCK cells and allantoic fluid were used as negative controls. The cells were incubated at 35° C. and CPE was observed. Using the Reed and Muench mathematical technique (17), the infectivity titer was expressed as $TCID_{50}/100$ µl and $1000 EID_{50}/200$ µl and the respective viruses were each diluted to having 100 $TCID_{50}$ and 500 $EID_{50}$ in 50 µl and 100 µl, respectively. Serially diluted mAbs 3B1 and 3E8 were able to neutralize the final concentration of $100 TCID_{50}$ and 500 $EID_{50}$ of virus (e.g. A/Indonesia/DCD669/H5N1) infecting MDCK cells and embryos. See Table 3. The numbers in Table 3 reflect the highest dilution ratio of H5N1 viruses at which the mAbs were still able to detect and neutralize the virus at a final concentration of 100 $TCID_{50}$ and 500 $EID_{50}$ of viruses in infected MDCK cells and chicken embryos.

TABLE 3

| | 3B1 | 3E8 |
|---|---|---|
| MDCK | 80 | 160 |
| 3mbryo | 20 | 40 |

Epitope Mapping.

1. Linear epitope or conformational epitope determination. Sodium dodecyl sulfate-polyacrylamide gel electrophoresis (SDS-PAGE) and Western blotting were used to identify linear epitopes of monoclonal antibodies. SDS-PAGE and Western blotting were performed as described by Ausubel et al. (18). The GST-tagged recombinant HA1 from H5N1 was expressed and subjected to 10% SDS-PAGE. Recombinant HA1 is about 32 kD, and the expressed GST-tagged HA1 is about 57 kD. The protein samples were prepared by mixing protein sample with sample buffer and heated at 100° C. for 5 minutes. After a brief spin, whole-cell lysate was loaded. Proteins separated by SDS-PAGE were visualized by staining with Coomassie Blue (0.25% Coomassie Brilliant Blue R-250, 40% methanol and 10% glacial acetic acid) for 30 minutes and then destained overnight in destaining solution (40% methanol and 10% glacial acetic acid). For Western blots, proteins were transferred from gel to a nitrocellulose membrane using a Transblot Cell (Bio-Rad). After elctrotransfer, the membrane was blocked with 5% non-fat milk in PBS-T and processed in the same manner as the dot blots above. The membrane was blocked with 5% non-fat milk (Bio-Rad, Canada) in PBS with 0.05% Tween-20 (PBS-t) for 60 minutes. After blocking, undiluted hybridoma culture fluid containing mAbs was incubated with the membrane for 60 minutes, washed with PBS-T and then incubated with goat anti-mouse horseradish peroxidase-conjugated antibodies (1:2000 dilution) (DakoCytomation) for 60 minutes. The membrane was washed and then developed with ECL Western blotting detection reagent (Amersham Biosciences) and exposed to KODAK Scientific imaging film (KODAK BioMAX MS, USA).

Neither of mAb 3B1 or mAb 3E8 reacted with recombinant HAL which indicated that the epitopes of these mAbs are conformational.

2. Selection of escape mutants and conformational/neutralizing epitopes mapping of H5 subtype mAbs. Serial 10-fold dilution of parental virus A/Indonesia/CDC669/H5N1 was mixed with an equal volume of mAb. After incubation of 1 hour at room temperature, the mixture was inoculated onto a monolayer of MDCK cells in DMEM medium containing 200 µg/ml TPCK-treated trypsin (Sigma) and 0.001% DEAE-dextran (Sigma). After 7 days at 35° C., the virus supernatant was collected and subject to further selection. The escape mutant was cloned and collected for RNA extraction. The point mutation responsible for the resistance to mAb neutralization was determined by sequence alignment with the parental virus. The ability of this mutation to allow the mutant virus to escape mAb neutralization was verified by neutralization assay and hemagglutinin inhibition assay.

An escape mutant was selected using neutralized mAb 3E8. The escape mutant was cloned and collected for RNA extraction. According to the sequence, the point mutation occurs on nucleotide 614 of the HA sequence (sequence available in GenBank; GenBank Accession #CY014481; GenBank GI #113497155). Nucleotide 614 "G" changes into "A," which results in mutation on amino acid 205 from arginine into lysine. Such mutation enables the mutant virus to escape antibody neutralization from mAb 3E8, which was verified with neutralization assays and hemagglutinin inhibition assay. This result indicated the mAb 3E8 targets the epitope containing amino acid 205 on hemagglutinin. Another neutralization epitope was identified for mAb 3B1 using the same method. The results are indicated in Table 4, which shows the location of mAb neutralization epitopes on the hemagglutinin molecule of AIV (A/Indonesia/CDC669/H5N1).

TABLE 4

Location of Neutralization Epitopes on Hemagglutinin Molecule of AIV (A/Indonesia/CDC669/H5N1) by mAbs

| Escape Mutant | Nucleotide | Nucleotide Change | Amino acid | Amino acid Change |
|---|---|---|---|---|
| 3B1 | 512 | G to T | 171 | Ser to Ile |
| 3E8 | 614 | G to A | 205 | Arg to Lys |

Prophylaxis and therapeutics. Based upon the neutralization ability to H5N1 on MDCK cells and chicken embryos, mAb 3B1 and mAb 3E8 can be used for prophylaxis. The variable region, eg., Fab, of anti-hemagglutinin monoclonal antibodies also can have therapeutic activity (21,22). Recombinant antibodies from mAb 3B1 and mAb 3E8 can have both prophylactic and therapeutic efficiency.

A recombinant antibody containing the variable region of mAb 3B1 was expressed and used in the HI test as follows:

Design of the expression vector for human IgG1 was based on that described by Jostock et al. (28) A synthetic secretion leader and the internal ribozome entry site (IRES) of encephalomyocarditis virus from pIREs (Clontech) were used to replace the multiple cloning site, myc-tag and constant regions, cDNA clones (I.M.A.G.E. Consortium cDNA clones [Lennon, G., et al. (29)]) encoding the Kappa light chain (Clone ID 6279986) and the IgG1 heavy chain (Clone ID 6281248) were amplified to allow insertion.

To isolate the cDNA encoding the variable regions of mAb 3B 1, mRNA was prepared from hybridoma cells and used in first strand cDNA synthesis with random hexanucleotides. The total cDNA then was used as template in reactions to amplify both the variable heavy and light chains using the primers and protocols of the mouse scFv recombinant antibody phage system (Amersham Biosciences, Piscataway, N.J.) with the resulting products cloned into pCR-Script (Stratagene) for sequencing. Variable region specific primers were used to amplify both the heavy and light chain variable regions to allow cloning into the constructed expression vector above. Expression of the resulting construct gave rise to a chimeric antibody containing the mouse variable and human constant regions.

Chimeric antibodies were expressed using the FreeStyle® 293 expression system (Invitrogen, Carlsbad, Calif.) to obtain antibody produced in a defined, serum-free medium. Constructs encoding chimeric IgG1 were transfected into 293-F cells by use of 293 fectin (Invitrogen). Supernatants were collected 120 hours after transfection and proteins purified using protein A sepharose beads (Amersham Biosciences). Purity of IgG was confirmed using SDS-PAGE analyses.

The purified chimeric antibody with human IgG1 constant region and murine variable region from mAB3B 1 was tested on H1 and H5N1. The HI activity was indicated in Table 5, below:

TABLE 5

Purified Recombinant mAb 3B1 HI Activity Test

| Virus isolates | H1 titer (at 0.1 mg/ml) |
|---|---|
| A/Indonesia/CDC329/H5N1 | 128 |
| A/Indonesia/CDC523/H5N1 | 512 |
| A/Indonesia/CDC594/H5N1 | 4 |
| A/Indonesia/CDC623/H5N1 | 64 |
| A/Indonesia/CDC644/H5N1 | 256 |
| A/Indonesia/CDC669/H5N1 | 128 |

The chimeric antibody with variable region from mAb 3B1 maintains affinity to AIV H5N1. In addition to the advantages of the original murine antibody, the chimeric antibody of IgG1 subtype with human constant region can be administered to humans for therapeutic treatment against H5-subtype AIV infection.

EXAMPLE 4

Antigen Capture ELISA (AC-ELISA) for H5N1 Subtype AIV Identification Using a Combination of mAb 6C6 Against N–1 Subtype and mAb 3B1 or 3E8 Against H5 Subtype Samples containing H5 virus can be verified as H5N1 through the use of a combination of mAb 3B1 or mAb 3E8 and mAb 6C6. An AC-ELISA is designed to detect H5N1 virus. MAb 3B1 or 3E8 is incubated at 0.5 mg/well in 100 µl PBS in a 96 well plate (U96 Maxisorp NUNC-immuno plate) overnight at 4° C. After rinsing the plate with PBS-T, the coated plate is blocked with 1% bovine serum albumin (BSA) for 1 hour at room temperature. The block soltion then is discarded and inactivated H5N1 isolates diluted in PBS at 20 HA units in 100 µl are added to each well and incubated for 2 hours. the plates are washed four times in wash buffer PBS-T, and 100 µl of horseradish peroxidase-labeled mAb 6C6 diluted 1/500 are added to each well. the plates are further incubated for 1 hour at room temperature and then washed six times with wash buffer. One hundred microliters of freshly prepared substrate (10 mg of o-phenylenediamine dihydrochloride per 20 ml of 0.05 M phosphate citrate buffer, pH 5.0, containing 0.03% sodium perborate) are added to each well and the plates are incubated at room temperature for approximately 5 minutes. The reaction is stopped with 50 µl of 2N sulfuric acid. The absorbance is measured at 490 nm ($A_{490}$) with an automated plate spectrophotometer (Mitenyi Biotec). A significant $A_{490}$ reading indicates that the virus is subtype H5N1. A sample containing H5N1 AIV can be identified using mAb 3B 1 or 3E8 and 6C6 separately, but using the antibodies in combination provides for determination using a smaller virus sample.

TABLE 6

Avian Influenza Virus A Isolates Used to Test mAb 3B1 and mAb 3E8 by IFA

| MAbs (target) | 3B1 (H5) | 3E8 (H5) |
| --- | --- | --- |
| A/Indonesia/chicken/H5N1 | + | + |
| A/Indonesia/CDC7/H5N1 | + | + |
| A/Indonesia/CDC326/H5N1 | + | + |
| A/Indonesia/CDC329/H5N1 | + | + |
| A/Indonesia/CDC370/H5N1 | + | + |
| A/Indonesia/CDC390/H5N1 | + | + |
| A/Indonesia/CDC523/H5N1 | + | + |
| A/Indonesia/CDC594/H5N1 | + | − |
| A/Indonesia/CDC623/H5N1 | + | + |
| A/Indonesia/CDC644/H5N1 | + | + |
| A/Indonesia/CDC669/H5N1 | + | + |
| A/Indonesia/TLL001/H5N1 | + | + |
| A/Indonesia/TLL002/H5N1 | + | + |
| A/Indonesia/TLL003/H5N1 | + | + |
| A/Indonesia/TLL004/H5N1 | + | + |
| A/Indonesia/TLL005/H5N1 | + | + |
| A/Indonesia/TLL006/H5N1 | + | + |
| A/Indonesia/TLL007/H5N1 | + | + |
| A/Indonesia/TLL008/H5N1 | + | + |
| A/Indonesia/TLL009/H5N1 | + | + |
| A/Indonesia/TLL010/H5N1 | + | + |
| A/Indonesia/TLL011/H5N1 | + | + |
| A/Indonesia/TLL012/H5N1 | + | + |
| A/Indonesia/TLL013/H5N1 | + | + |
| H5N1/PR8 | + | − |
| A/chicken/Singapore/98 (H5N2) | + | − |
| H7N1/SG | − | − |
| H3N2 | − | − |
| H9N2 | − | − |
| H10N5 | − | − |

Note:
"+" means positive,
"−" indicates negative

Bibliography

1. Jeffery K. Taubenberger, Ann H. Reidl, Raina M. Lourensl, Ruixue Wang, Guozhong Jin and Thomas G. Fanningl. 2006. Molecular virology: Was the 1918 pandemic caused by a bird flu? Was the 1918 flu avian in origin? Nature. 440:E9-E10.

2. Ann H. Reid, Jeffery K. Taubenberger & Thomas G. Fanning 2004. Evidence of an absence: the genetic origins of the 1918 pandemic influenza virus. Nature Reviews Microbiology 2:909-914.

3. Patrick J Gavin, Richard B Thomson, Jr. 2003. Review of Rapid Diagnostic Tests for Influenza. Clinical and Applied Immunology Reviews 4:151-172.

4. Gregory A. Storch, M D. Rapid diagnostic tests for influenza. 2003. Current Opinion in Pediatrics. 15:77-84.

5. Yuen K Y, Chan P K, Peiris M, Tsang D N, Que T L, Shortridge K F, et al. 1998. Clinical features and rapid viral diagnosis of human disease associated with avian influenza A H5N1 virus. Lancet. 351:467-71.

6. Varghese, J. N. et al. 1998. Drug design against a shifting target: a structural basis for resistance to inhibitors in a variant of influenza virus neuraminidase. Structure 6:735-746.

7. Le, Q. M. et al. 2005. Avian flu: isolation of drug-resistant H5N1 virus. Nature 438: 754.

8. Kiso, M. et al. 2004. Resistant influenza A viruses in children treated with oseltamivir: descriptive study. Lancet 364:759-765.

9. de Jong, M. D. et at. 2005. Oseltamivir resistance during treatment of influenza A (H5N1) infection. N. Engl. J. Med. 353:2667-2672.

10. Russell R J, Haire L F, Stevens D J, Collins P J, Lin Y P, Blackburn G M, Hay A J, Gamblin S J, Skehel J J. 2006. The structure of H5N1 avian influenza neuraminidase suggests new opportunities for drug design. Nature 443, 45-49.

11. Cameron P Simmons, Nadia L Bernasconi, Amorsolo L Suguitan, Jr., Kimberly Mills, Jerrold M Ward, Nguyen Van Vinh Chau, Tran Tinh Hien, Federica Sallusto, Do Quang Ha, Jeremy Farrar, Menno D de Jong, Antonio Lanzavecchia, and Kanta Subbarao. 2007. Prophylactic and Therapeutic Efficacy of Human Monoclonal Antibodies against H5N1 Influenza. PLoS Med. 4:e178.

12. Brendon J Hanson, Adrianus C M Boon, Angeline P C Lim, Ashley Webb, Eng Eong Ooi, and Richard J. Webby. 2006. Passive immunoprophylaxis and therapy with humanized monoclonal antibody specific for influenza A H5 hemagglutinin in mice. Respir Res. 7: 126.

13. Jiahai Lu, Zhongmin Guo, Xinghua Pan, Guoling Wang, Dingmei Zhang, Yanbin Li, Bingyan Tan, Liping Ouyang, and Xinbing Yu. 2006. Passive immunotherapy for influenza A H5N1 virus infection with equine hyperimmune globulin F(ab')2 in mice. Respir Res.; 7: 43.

14. Chen H, Smith G J, Li K S, Wang J, Fan X H, Rayner J M, Vijaykrishna D, Zhang J X, Zhang U, Guo C T, Cheung C L, Xu K M, Duan L, Huang K, Qin K, Leung Y H, Wu W L, Lu H R, Chen Y, Xia N S, Naipospos T S, Yuen K Y, Hassan S S, Bahri S, Nguyen T D, Webster R G, Peiris J S, Guan Y. 2006. Establishment of multiple sublineages of H5N1 influenza virus in Asia: implications for pandemic control. Proc Natl Acad Sci USA. 103:2845-50.

15. Smith G J, Naipospos T S, Nguyen T D, de Jong M D, Vijaykrishna D, Usman T B, Hassan S S, Nguyen T V, Dao T V, Bui N A, Leung Y H, Cheung C L, Rayner J M, Zhang J X, Zhang U, Poon L L, Li K S, Nguyen V C, Hien T T, Farrar J, Webster R G, Chen H, Peiris J S, Guan Y. 2006. Evolution and adaptation of H5N1 influenza virus in avian and human hosts in Indonesia and Vietnam. Virology. 350:258-68.

16. De St. Groth, S. F., and D. Scheidigger. 1980. Production of monoclonal antibodies. Strategy and tactics. J. Immunol. Methods. 35:121.

17. Reed, L. J., and H. Muench. 1938. A simple method of estimating fifty percent endpoints, Am. J. Hyg. 27:493-497.

18. Ausubel, F. M., Brent, R., Kingston, R. E., Moore, D. D., Seidman, J. G., Smith, J. A. and K. Struhl. 1999. Current protocols in molecular biology. John Wiley and Sons, Inc., New York, N.Y.

19. Yuichi Harada, Masamichi Muramatsu, Toshikatsu Shibata, Tasuku Honjo, and Kazumichi Kuroda. Unmutated hnmunoglobulin M Can Protect Mice from Death by Influenza Virus Infection. J. Exp. Med. 197: 1779-1785.

20. Palladino, G, Mozdzanowska, K, Washko, G, Gerhard, W. 1995. Virus-neutralizing antibodies of immunoglobulin G (IgG) but not of IgM or IgA isotypes can cure influenza virus pneumonia in SCID mice. J. Virol. 69:2075-2081.

21. Krystyna Mozdzanowska, Jingqi Feng, and Walter Gerhard. J. 2003. Virus-Neutralizing Activity Mediated by the Fab Fragment of a Hemagglutinin-Specific Antibody Is Sufficient for the Resolution of Influenza Virus Infection in SCID Mice. J. Virol. 77:8322-8328.

22. Lu J, Guo Z, Pan X, Wang G, Zhang D, Li Y, Tan B, Ouyang L, Yu X. 2006. Passive immunotherapy for influenza A H5N1 virus infection with equine hyperimmune globulin F(ab')2 in mice. Respiratory Research. 7:43.

23. Zhou, N. N. et al. 1999. Genetic reassortment of avian, swinw, and human influenza A viruses in American pig: Virol. 73:8851-6.

24. Horimoto, T. et al. Antigenic differences between H5N1 human influenza viruses isolsted in 1997 and 2003. *J. Vet. Med. Sci.* 66:303-5.

25. Iwasaki, T., et al. *Acta Neuropathol. (Berl).*, 108:485-92.

26. Steven, J, et al. Structure and receptor specificity of the hemagglutinin from an H5N1 influenza virus. *Science* 312: 404-10.

27. Robert G. Webster, A. G. 1994. *Encyclopedia of Virology,* 2:709-724.

28. Jostock, T. et al., 2004. *J. Immunol. Methods* 289(1-2): 65-80.

29. Lennon G., Auffray, C., Polymeropoulos, M., Soares, M B, "The I.M.A.G.E. Consortium: an integrated molecular analysis of genomes and their expression," Genomics, 1996, 33(1): 151-152.

The invention claimed is:

1. An antibody or antibody fragment that binds specifically to a conformational epitope of the envelope glycoprotein hemagluttinin of an H5subtype of avian influenza virus that has substantially the immunological binding characteristics of monoclonal antibody 3B1 as produced by hybridoma 3B1 which is deposited with the American Type Culture Collection with Accession Number PTA-8247, wherein said immunological binding characteristics comprise binding to an epitope that is bound by monoclonal antibody 3B1.

2. The antibody or antibody fragment of claim 1 which is a monoclonal antibody, a single chain antibody, an antibody fragment, a chimeric antibody or a humanized antibody.

3. The antibody or antibody fragment of claim 1 which is a monoclonal antibody.

4. Monoclonal antibody 3B1 as produced by hybridoma 3B1 which is deposited with the American Type Culture Collection with Accession Number PTA-8247.

5. A method for detecting H5 subtype avian influenza virus in a biological specimen which comprises contacting the specimen with a first antibody or antibody fragment that binds specifically to a conformational epitope of the envelope glycoprotein hemagluttinin of an H5 subtype of avian influenza virus said first antibody or antibody fragment having substantially the immunological binding characteristics of monoclonal antibody 3B1 as produced by hybridoma 3B1 which is deposited with the American Type Culture Collection with Accession Number PTA-8247, wherein said immunological binding characteristics comprise binding to an epitope that is bound by monoclonal antibody 3B1.

6. The method of claim 5, wherein the first antibody or antibody fragment is a monoclonal antibody, a single chain antibody, an antibody fragment, a chimeric antibody or a humanized antibody.

7. The method of claim 5, wherein the first antibody or antibody fragment is a monoclonal antibody.

8. The method of claim 5 which further comprises contacting the specimen with a second antibody or antibody fragment that specifically binds to the envelope glycoprotein of an H5 subtype of avian influenza virus, wherein the first antibody or antibody fragment is a capture antibody or antibody fragment and the second antibody or antibody fragment is a detector antibody or antibody fragment that contains or is conjugated to a detectable element.

9. The method of claim 8 wherein at least one of the first and second antibody or antibody fragments is a monoclonal antibody.

10. The method of claim 8 wherein the first and second antibody or antibody fragment are monoclonal antibodies.

11. The method of claim 8 wherein the first antibody or antibody fragment is immobilized onto a solid surface.

12. The method of claim 8 wherein the second antibody or antibody fragment contains a radioactive atom, is conjugated to a fluorescent molecule, or is conjugated to an enzyme.

13. A method for detecting H5N1 subtype avian influenza virus in a biological specimen which comprises contacting the specimen with a first antibody or antibody fragment that binds to a conformational epitope of the envelope glycoprotein hemagluttinin of an H5 subtype of avian influenza virus, said first antibody or antibody fragment having substantially the immunological binding characteristics of monoclonal antibody 3B1 as produced by hybridoma 3B1 which is deposited with the American Type Culture Collection with Accession Number PTA-8247, wherein said immunological binding characteristics comprise binding to an epitope that is bound by monoclonal antibody 3B1, and with a second antibody or antibody fragment that binds to the neuraminidase glycoprotein of an N1 subtype of avian influenza virus, said second binding protein having substantially the immunological binding characteristics of monoclonal antibody 6C6 as produced by hybridoma 6C6 which is deposited with the American Type Culture Collection with Accession Number PTA-8526, wherein said immunological binding characteristics comprise binding to an epitope that is bound by monoclonal antibody 6C6.

14. A kit for detecting H5 subtype avian influenza virus in a biological specimen which comprises a first antibody or antibody fragment that binds specifically to a conformational epitope of the envelope glycoprotein hemagluttinin of an H5 subtype of avian influenza virus said first antibody or antibody fragment having substantially the immunological binding characteristics of monoclonal antibody 3B1 as produced by hybridoma 3B1 which is deposited with the American Type Culture Collection with Accession Number PTA-8247, wherein said immunological binding characteristics comprise binding to an epitope that is bound by monoclonal antibody 3B1 together with reagents for the detection of binding of said first antibody or antibody fragment to said envelope glycoprotein.

15. The kit of claim 14 which comprises a second antibody or antibody fragment that specifically binds to the envelope glycoprotein of an H5subtype of avian influenza virus, wherein the first antibody or antibody fragment is a capture antibody or antibody fragment and the second antibody or antibody fragment is a detector antibody or antibody fragment that contains or is conjugated to a detectable element.

16. The kit of claim 15 wherein at least one of the first and second antibody or antibody fragments is a monoclonal antibody.

17. The kit of claim 15 wherein the first and second antibody or antibody fragment are monoclonal antibodies.

18. The kit of claim 15 wherein the first antibody or antibody fragment is immobilized onto a solid surface.

19. The kit of claim 15 wherein the second antibody or antibody fragment contains a radioactive atom, is conjugated to a fluorescent molecule, or is conjugated to an enzyme.

20. The kit of claim 14 which further comprises a second antibody or antibody fragment that binds to a conformational epitope of the neuraminidase glycoprotein of an N1 subtype of avian influenza virus said second antibody or antibody fragment having substantially the immunological binding characteristics of monoclonal antibody 6C6 as produced by hybridoma 6C6which is deposited with the American Type Culture Collection with Accession Number PTA-8526, wherein said immunological binding characteristics comprise binding to an epitope that is bound by monoclonal antibody 6C6.

21. A method of treating a subject infected with H5 subtype avian influenza virus which comprises administering to said subject an effective amount of a antibody or antibody fragment that binds specifically to a conformational epitope of the envelope glycoprotein hemagluttinin of an H5 subtype of avian influenza virus that has substantially the immunological binding characteristics of monoclonal antibody 3B1 as produced by hybridoma 3B1 which is deposited with the American Type Culture Collection with Accession Number PTA-8247, wherein said immunological binding characteristics comprise binding to an epitope that is bound by monoclonal antibody 3B1.

22. The method of claim 21, wherein the antibody or antibody fragment is a recombinant monoclonal antibody, single chain antibody, antibody fragment, chimeric antibody or humanized antibody.

23. The method of claim 22, wherein the antibody or antibody fragment is a recombinant monoclonal antibody comprising the variable region of mAb 3B1.

* * * * *